United States Patent [19]

Torii et al.

[11] Patent Number: 5,142,040
[45] Date of Patent: Aug. 25, 1992

[54] PROCESS FOR PREPARING A 3-FORMYLCEPHEM DERIVATIVE

[75] Inventors: Sigeru Torii; Hideo Tanaka, both of Okayama; Masatoshi Taniguchi, Tokushima; Michio Sasaoka, Tokushima; Takashi Shiroi, Tokushima; Ryo Kikuchi, Tokushima; Yutaka Kameyama, Tokushima, all of Japan

[73] Assignee: Otsuka Kagaku Kabushiki Kaisha, Osaka, Japan

[21] Appl. No.: 665,838

[22] Filed: Mar. 7, 1991

[30] Foreign Application Priority Data

Mar. 8, 1990 [JP] Japan .................................. 2-56955

[51] Int. Cl.⁵ ............................................. C07D 501/04
[52] U.S. Cl. .................... 540/222; 540/215; 540/230
[58] Field of Search ........................ 540/230, 222, 228

[56] References Cited

U.S. PATENT DOCUMENTS 4,269,977  5/1981  Peter et al. .......................... 540/215

FOREIGN PATENT DOCUMENTS 46-20707   6/1971  Japan .
47-933     1/1972  Japan .
5071691   11/1973  Japan .
49-80097   8/1974  Japan .
51-122087 10/1976  Japan .

OTHER PUBLICATIONS

Helvetica Chimica Acta, vol. 57, Fasc. 7 (1974)–Nr. 219 (German).

Japan Medical Chemistry, 10(5), 1967.
Chem. Pharm. Bull. 28(4) 1339–1341 (1980), "A New Synthetic Method of 3-Formylcephalosporins".
Chemical Abstracts vol. 115(21):231989(p) (1991).
Chemical Abstracts vol. 114(5) 42319p (1991).
Chemical Abstracts vol. 105(11) 97207v (1986).

Primary Examiner—Nicholas S. Rizzo
Attorney, Agent, or Firm—Armstrong & Kubovcik

[57] ABSTRACT

The present invention provides a process for preparing a 3-formylcephem derivative represented by the formula (2)

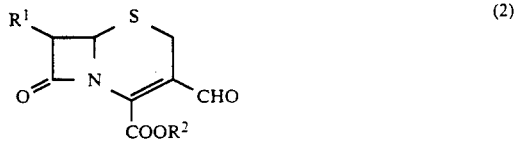

which comprises oxidizing in the presence of oxygen a 3-halomethylcephem derivative represented by the formula (1)

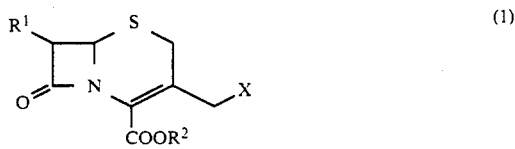

wherein $R^1$ is amino group or protected amino group, $R^2$ is hydrogen atom or a carboxylic acid protective group, X is halogen atom.

3 Claims, No Drawings

PROCESS FOR PREPARING A 3-FORMYLCEPHEM DERIVATIVE

The present invention relates to a process for preparing a 3-formylcephem derivative.

The following methods are conventionally known as a method of preparing a 3-formylcephem derivative represented by the formula (2)

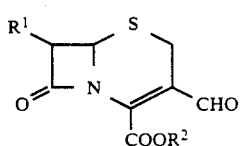

wherein $R^1$ is amino group or protected amino group, $R^2$ is hydrogen atom or a group protecting carboxylic acid (carboxylic acid protective group).

(A) A method of oxidizing a 3-hydroxymethyl-3-cephem derivative [i ) dimethylsulfoxide-acetic anhydride; Helv. Chim. Acta, 57, 2044(1974), JP-A-47-933, ii ) $MnO_2$; J. Med. Chem., 10(5), 966(1967), iii) $Cr^{6+}$; JP-B-46-20707, JP-A-49-80097, JP-A-50-71691], (B) A method of oxidizing a 3-halomethyl-2(or 3)-cephem derivative [JP-A-51-122087], and (C) A method of oxidizing a 3'-bromolactonecephem derivative [Chem. Pharm. Bull., 28, 1339(1980)], etc.

However, method A involves side reactions such as isomerization of a double bond in the cephem ring ($\Delta^3 \rightarrow \Delta^2$) or forming of a lactone skeleton. Further, several reaction steps are necessary for preparing a starting 3-hydroxymethyl-3-cephem derivative. Therefore, complicated isolation or purification steps are required for obtaining a desired compound, which entails a drawback of lowering a yield. Whereas, method B has drawbacks of using an expensive AgF-dimethylsulfoxide as an oxidizing agent and providing only 3-formyl-2-cephem compound as a product. Further, method C has drawbacks of requiring several reaction steps for preparing a 3'-bromolactonecephem derivative and of being low in a yield of a desired product.

An object of the present invention is to provide a process for preparing a 3-formylcephem derivative in a high yield and high purity which is free from drawbacks of the above conventional methods, and is industrially advantageous with safe and simple steps using an easily available 3-halomethylcephem derivative as a starting compound.

The present invention provides a process for preparing a 3-formylcephem derivative represented by the formula (2)

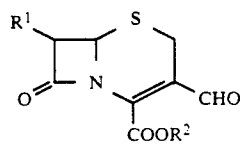

which comprises oxidizing in the presence of oxygen a 3-halomethylcephem derivative represented by the formula (1)

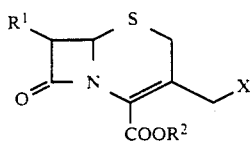

wherein $R^1$ is amino group or protected amino group, $R^2$ is hydrogen atom or a carboxylic acid protective group, X is halogen atom.

The 3-formylcephem derivative obtained in the present invention is useful, for example, as an intermediate of β-lactam antibiotics.

In the present invention, 3-formylcephem derivative of the formula (2) can be prepared by a simple method in a high yield and high purity which comprises oxidizing 3-halomethylcephem derivative of the formula (1) in the presence of oxygen.

In the present specification, X is halogen atom such as Cl, Br and I, and is preferably iodine atom. Examples of protected amino groups represented by R' are phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-t-butylbenzamido, p-methoxybenzamido, p-chlorobenzamido and p-bromobenzamido groups. The following groups are also enumerated.

Groups described in Chapter 7 (p218~287) of "Protective Groups in Organic Synthesis" by Theodora W. Greene.

Phenylglycylamido group and phenylglycylamido group in which amino group is protected.

p-Hydroxyphenylglycylamido group and p-hydroxyphenylglycylamido group in which amino, hydroxy or both of them are protected. Examples of protective groups for amino group of phenylglycylamido and p-hydroxyphenylglycylamido groups are those described in Chapter 7 (p218~287) of "Protective Groups in Organic Synthesis" by Theodora W. Greene. Examples of protective groups for hydroxyl group of p-hydroxyphenylglycylamido group are those described in Chapter 2 (p10~72) of "Protective Groups in Organic Synthesis" by Theodora W. Greene.

Examples of carboxylic acid protective groups are benzyl group, p-methoxybenzyl group, p-nitrobenzyl group, diphenylmethyl group, trichloroethyl group, t-butyl group or those described in Chapter 5 (p152~192) of "Protective Groups in Organic Synthesis" by Theodora W. Greene.

In the present invention, the 3-halomethylcephem derivative of the above formula (1) is oxidized in the presence of oxygen or air, when necessary at a pressure of 0.01 to 20 $kg/cm^2$, preferably 0.01 to 10 $kg/cm^2$ of oxygen or air. The reaction is conducted preferably in an organic solvent. As the organic solvent are used those which dissolve the compound of the formula (1) and are inert at the reaction condition. Preferable solvent are dimethylformamide, dimethylacetamide and like amides. The solvent is used in an amount of about 0.5 to 100 l, preferably about 1 to 20 l per 1 kg of the compound of the formula (1).

The reaction temperature varies in its preferable range depending on a starting material, oxygen pressure or the like, and is usually about $-10°$ to $80°$ C., preferably $0°$ to $50°$ C. Although the reaction proceeds usually in the presence of oxygen, it is possible, in order to complete the reaction at lower temperature and in shorter period of time, to add an additive such as starch; trimethyl phosphite, triethyl phosphite, tributyl phosphite, triphenyl phosphite or like phosphites; rhodium (III) oxide, rhodium (III) chloride, rhodium (III) acetylacetonate, rhodium (II) acetate dimer or like rhodium salts; vanadium (III) acetylacetonate, vanadium (III) chloride, vanadium (III) trioxide, vanadium (IV) tetroxide, vanadium (V) pentoxide, vanadyl acetylacetonate, vanadyl sulfate, vanadyl oxalate or like vanadium salts, etc. The additive is used in an amount of preferably 0.0001 to 5 moles per mole of the compound of the formula (1).

In the present invention, after the completion of the reaction, the desired 3-formylcephem derivative of the formula (2) can be isolated for example by a usual extraction. When required, the compound can be purified by a usual means such as recrystallization, column chromatography or the like.

In the present invention, the desired 3-formylcephem derivative of the formula (2) can be prepared by a very simple manner and in a high yield using an industrially easily available 3-halomethylcephem derivative of the formula (1) as a starting material.

The invention is described in more details with reference to examples in which Ph is phenyl group and t-Bu is tert-butyl group.

EXAMPLE 1

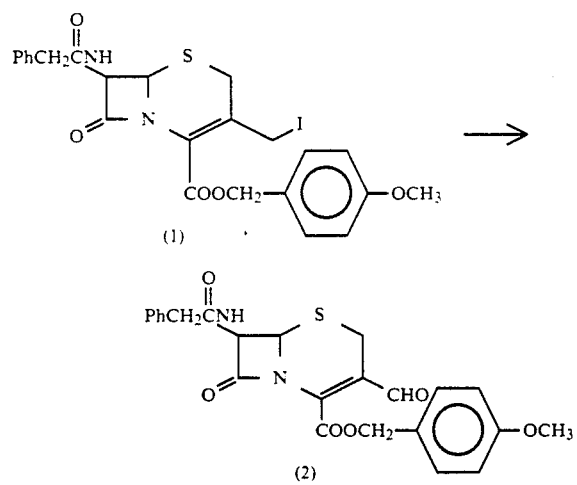

The compound 1 (1 g) was dissolved in dimethylformamide (10 ml). The solution was placed in an autoclave and oxygen was added thereto at a pressure of 2.5 kg/cm$^2$. The solution was reacted at room temperature for 2 hours with stirring. Water was added to the reaction mixture which was then extracted with ethyl acetate. The extract was washed with water, dried over anhydrous MgSO$_4$, and then concentrated at a reduced pressure. The resulting residue was purified by a silica gel column chromatography to obtain the compound 2 in a yield of 60%.

NMR(CDCl$_3$); δ ppm 3.24, 3.96(ABq, 2H, J=18Hz), 3.63, 3.68(ABq, 2H, J=16 Hz), 3.80(s, 3H), 4.98(d, 1H, J=5 Hz), 5.27, 5.30(ABq, 2H, J=11 Hz), 5.95(dd, 1H, J=5Hz,9Hz), 6.04(d, 1H, J=9Hz), 6.90(d, 1H, J=6Hz), 7.20~7.40(m, 7H), 9.79(s, 1H)

EXAMPLE 2

The compound 1 (1 g) was dissolved in dimethylformamide (10 ml). The solution was placed in an autoclave and vanadyl acetylacetonate (0.1 g) was added thereto. Oxygen was added thereto at a pressure of 5 kg/cm$^2$. The solution was reacted at room temperature for 1 hour with stirring. Water was added to the reaction mixture which was then extracted with ethyl acetate. The extract was washed with water, dried over anhydrous MgSO$_4$ and then concentrated at a reduced pressure. The resulting residue was purified by a silica gel column chromatography to obtain the compound 2 in a yield of 90%.

EXAMPLE 3

The compound 1 (1 g) was dissolved in dimethylformamide (10 ml). The solution was placed in an autoclave and rhodium chloride (10 mg) was added thereto. Oxygen was added thereto at a pressure of 5 kg/cm$^2$. The solution was reacted at room temperature for 2 hours with stirring. Water was added to the reaction mixture which was then extracted with ethyl acetate. The extract was washed with water, dried over anhydrous MgSO$_4$ and then concentrated at a reduced pressure. The resulting residue was purified by a silica gel column chromatography to obtain the compound 2 in a yield of 80%.

EXAMPLES 4 to 7

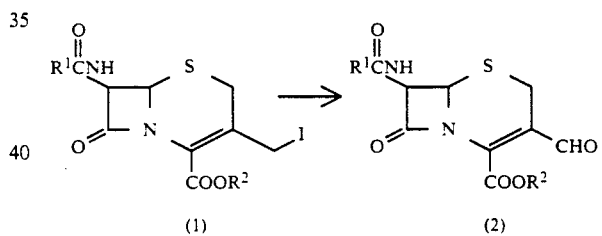

The compound of the above formula (2) was prepared from the compound of the above formula (1) in the same manner as in Example 2. The detail of the compounds and the reaction condition were given in Table 1. The NMR spectra of these desired compound were consistent with those of the compound (2) which was prepared in another method.

TABLE 1

| R$^1$ | R$^2$ | pressure of oxygen | reaction time | yield |
|---|---|---|---|---|
| —CH$_2$—(thiophene) | CH$_3$ | 5 kg/cm$^2$ | 1 hr | 85% |
| —CH$_2$—(thiophene) | CHPh$_2$ | 5 kg/cm$^2$ | 1 hr | 90% |
| (phenyl)—t-Bu | CHPh$_2$ | 5 kg/cm$^2$ | 1 hr | 85% |

TABLE 1-continued

| $R^1$ | $R^2$ | pressure of oxygen | reaction time | yield |
|---|---|---|---|---|
| —CH—Ph<br>  \|<br>  NHCOOBu-t | CHPh$_2$ | 5 kg/cm$^2$ | 1 hr | 80% |

We claim:

1. A process for preparing a 3-formylcephem derivative represented by the formula (2)

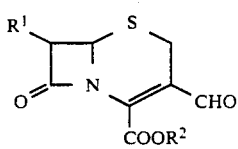
(2)

which comprises oxidizing in the presence of oxygen a 3-halomethylcephem derivative represented by the formula (1)

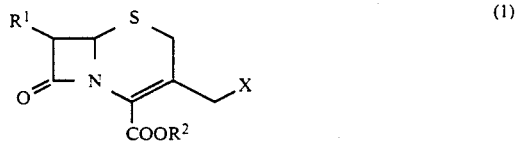
(1)

wherein $R^1$ is amino group or protected amino group, $R^2$ is hydrogen atom or a carboxylic acid protective group, X is halogen atom.

2. The process according to claim 1, wherein the oxidizing step is performed at a pressure of 0.01 to 20 kg/cm$^2$.

3. The process according to claim 1, wherein the oxidizing step is performed at a reaction temperature from about $-10°$ to 80° C.

* * * * *